US008961613B2

(12) United States Patent
Assell et al.

(10) Patent No.: US 8,961,613 B2
(45) Date of Patent: Feb. 24, 2015

(54) LOW FRICTION RESURFACING IMPLANT

(71) Applicant: Zyga Technology, Inc., Minneapolis, MN (US)

(72) Inventors: Robert L. Assell, St. Paul, MN (US); Brian P. Beaubien, St. Paul, MN (US); David W. Stassen, Edina, MN (US)

(73) Assignee: Zyga Technology, Inc., Minneapolis, MN (US)

( * ) Notice: Subject to any disclaimer, the term of this patent is extended or adjusted under 35 U.S.C. 154(b) by 0 days.

(21) Appl. No.: 13/678,516

(22) Filed: Nov. 15, 2012

(65) Prior Publication Data

US 2014/0135938 A1    May 15, 2014

Related U.S. Application Data

(63) Continuation-in-part of application No. 12/898,285, filed on Oct. 5, 2010.

(60) Provisional application No. 61/249,447, filed on Oct. 7, 2009.

(51) Int. Cl.
*A61B 17/70* (2006.01)
*A61F 2/38* (2006.01)
*A61F 2/30* (2006.01)

(52) U.S. Cl.
CPC ........ *A61F 2/3872* (2013.01); *A61F 2002/3008* (2013.01); *A61F 2002/30322* (2013.01); *A61F 2002/30754* (2013.01); *A61F 2002/30841* (2013.01)
USPC .................. 623/20.31; 623/20.14; 623/20.28; 623/20.3; 606/60

(58) Field of Classification Search
USPC ...................... 623/14.12, 16.11, 17.11, 17.15, 623/20.14–20.16, 20.28–20.33; 606/246–249, 279
See application file for complete search history.

(56) References Cited

U.S. PATENT DOCUMENTS

| | | | |
|---|---|---|---|
| 5,702,463 A | 12/1997 | Pothier et al. | |
| 6,468,314 B2 | 10/2002 | Schwartz et al. | |
| 7,875,080 B2 * | 1/2011 | Puno et al. .................. | 623/17.16 |
| 8,394,125 B2 * | 3/2013 | Assell et al. .................. | 606/247 |
| 2004/0133275 A1 | 7/2004 | Mansmann | |
| 2006/0235517 A1 | 10/2006 | Hodorek | |
| 2007/0067032 A1 | 3/2007 | Felt et al. | |
| 2007/0149982 A1 | 6/2007 | Lyons | |
| 2007/0233269 A1 | 10/2007 | Steines et al. | |
| 2008/0183291 A1 | 7/2008 | Scheller et al. | |
| 2009/0088846 A1 | 4/2009 | Myung et al. | |
| 2011/0022089 A1 | 1/2011 | Assell et al. | |
| 2011/0082548 A1 * | 4/2011 | Assell et al. ............... | 623/14.12 |
| 2011/0307061 A1 | 12/2011 | Assell et al. | |

OTHER PUBLICATIONS

International Search Report (PCT/US2013/070072) dated Apr. 23, 2014—21 pages.

* cited by examiner

*Primary Examiner* — Yashita Sharma
(74) *Attorney, Agent, or Firm* — Dicke, Billig & Czaja, PLLC

(57) ABSTRACT

A low friction resurfacing implant system including a first implant component having a first bearing surface and a first engagement surface. The first engagement surface is located opposite the first bearing surface. The first implant component has a leading edge and a trailing edge. The first implant component includes teeth that extend from the first engagement surface. The teeth are arranged in a plurality of rows. The teeth in adjacent rows are offset from each other.

14 Claims, 9 Drawing Sheets

LOW FRICTION RESURFACING IMPLANT

REFERENCE TO RELATED APPLICATION

This application is a continuation-in-part of U.S. application Ser. No. 12/898,285, which was filed on Oct. 5, 2010, which claimed priority to U.S. Provisional Application No. 61/249,447, which was filed on Oct. 7, 2009, the contents of which are incorporated herein by reference.

FIELD OF THE INVENTION

The present invention relates to orthopedic medicine, and more specifically to minimally-invasive tissue sparing implantable prostheses, associated tools, and methods for the resurfacing of articulating joints.

BACKGROUND OF THE INVENTION

The hip, knee, ankle and intervertebral discs of the spine are considered load-bearing joints, while the fingers and toes are considered non-weight bearing joints. The hip, knee, and ankle are further categorized as synovial joints, while the intervertebral discs are cartilaginous joints. These joints, especially the weight bearing joints, can undergo degenerative changes due to disease, age, trauma, repetitive loading and/or genetics.

For synovial joints, these degenerative changes come in the form of arthritis, or inflammation of the joint, leading to damage of the articular cartilage. Osteoarthritis mainly damages the joint cartilage, but there is often some inflammation as well. Rheumatoid arthritis is mainly inflammatory, and can eventually destroy the joint cartilage and adjacent bone. Fracture and other forms of trauma such as from sports injuries may also lead to degenerative changes.

Osteonecrosis is a condition in which either the bone of the femoral head or femoral condyles dies. The dead bone cannot withstand the stresses of walking and as a consequence, the femoral head or condyles then collapse, become irregular in shape, and cause pain in the hip or knee joints.

Osteoarthritis (OA) is the most common of the rheumatologic musculoskeletal disorders affecting about 21-26 million of the US adult population with the knee accounting for about 6.5 million of these cases.

Once the articular cartilage becomes deteriorated from OA, the result is bone rubbing against bone. The bone-on-bone friction causes discomfort ranging from feelings of stiffness to debilitating pain and eventual loss of motion.

Treatments for OA of the knee include conservative or non-pharmacological therapy, like physiotherapy, weight management and exercise; and more generally, intra-articular injections, arthroscopic surgery and knee replacement surgery. Whereas total or partial knee replacement surgery is considered an end-of-line intervention, the less invasive surgical procedures of lavage or debridement may be recommended for earlier and more severe disease.

Both arthroscopic lavage and debridement have been performed in patients with knee joint pain, with or without mechanical problems, refractory to medical therapy.

However arthroscopic lavage and debridement for osteoarthritis of the knee is still considered experimental and investigational by insurance companies because its effectiveness has not been established.

At this time, options that help to completely relieve severe osteoarthritis, include joint replacement or fusion. As examples, approximately 200,000 total knee joint and over 300,000 hip joint replacement operations are performed annually, and typically these artificial joints only last about 10-15 years.

Progression through the clinical pathway, however, is not linear, with treatment dependent on factors such as disease severity, patient preference, medical insurance reimbursement issues, and even the medical specialty of the physician the patient sees. In addition, some patients prefer not to have invasive surgery such as knee replacement; instead, they would prefer the less invasive injections and/or arthroscopic procedures.

It is therefore the object of the invention to provide a knee resurfacing implant, system, and method for treating patients experiencing moderate to severe OA knee pain who are either too young or too old to be candidates for total knee replacement surgery.

More particularly, the present invention relates to implantable systems, and corresponding insertion methods and procedures, which provide resurfacing of the knee joint anatomy on a minimally-invasive basis without bone resection and minimal native tissue disruption to reduce or eliminate joint pain and reestablish or maintain normal or near-normal joint stabilization and motion.

SUMMARY OF THE INVENTION

An embodiment of the invention is directed to a low friction resurfacing implant system that includes a first implant component having a first bearing surface and a first engagement surface. The first engagement surface is located opposite the first bearing surface.

The first implant component has a leading edge and a trailing edge. The first implant component includes teeth that extend from the first engagement surface. The teeth are arranged in a plurality of rows. The teeth in adjacent rows are offset from each other.

Another embodiment of the invention is directed to a low friction resurfacing implant system that includes a first implant component having a first bearing surface and a first engagement surface. The first engagement surface is located opposite the first bearing surface.

The first implant component includes a first plurality of teeth and a second plurality of teeth that extend from the first engagement surface. The first plurality of teeth has a first width. The second plurality of teeth has a second width and wherein the first width is greater than the second width.

Another embodiment of the invention is directed to a low friction resurfacing implant system that includes a first implant component having a first bearing surface and a first engagement surface located opposite the first bearing surface. The first implant component has a leading edge and a trailing edge.

The first implant component includes an insertion axis that extends between the leading edge and the trailing edge. The first implant component has teeth that extend from the first engagement surface. The teeth proximate the leading edge have a depth that is greater than a depth of the teeth proximate the trailing edge. The depth is in a direction that is aligned with the insertion axis.

Another embodiment of the invention is directed to a low friction resurfacing implant system that includes a first implant component having a first bearing surface, a first visualization marker, a leading edge, a trailing edge, a first opposing side and a second opposing side.

The first opposing side and the second opposing side extend between the leading edge and the trailing edge. The first visualization marker is mounted with respect to the first bearing surface and includes a first marker section and a second marker section. The first marker section is oriented at an angle with respect to the second marker section.

Another embodiment of the invention is directed to a low friction resurfacing implant system that includes a first implant component and a second implant component. The first implant component has a first bearing surface and a first visualization marker. The first visualization marker is mounted with respect to the first bearing surface.

The second implant component has a second bearing surface and a second visualization marker. The second visualization marker is mounted with respect to the second bearing surface. When the first implant component and the second implant component are placed in an implantation configuration with the first bearing surface adjacent to the second bearing surface, the first visualization marker and the second visualization marker indicate location and orientation of the first implant component and the second implant component.

Another embodiment of the invention is directed to a method of resurfacing a joint with a low friction resurfacing implant system. The joint includes a first bone and a second bone that are adjacent to each other and movable with respect to each other.

A first implant component is provided that includes a first bearing surface and a first engagement surface located opposite the first bearing surface. The first implant component has teeth that extend from the first engagement surface. The teeth are arranged in a plurality of rows so that teeth in adjacent rows are offset from each other.

The first implant component is implanted so that the teeth are at least partially embedded into tissue on the first bone. The offset teeth in the adjacent rows cause the first implant component to resist movement with respect to the first bone after implantation.

Another embodiment of the invention is directed to a method of resurfacing a joint with a low friction resurfacing implant system. The joint includes a first bone and a second bone that are adjacent to each other and movable with respect to each other.

A first implant component is provided that includes a first bearing surface and a first engagement surface located opposite the first bearing surface. The first implant component includes a first plurality of teeth and a second plurality of teeth that extend from the first engagement surface. The first plurality of teeth has a first width. The second plurality of teeth has a second width. The first width is greater than the second width.

The first implant component is implanted so that the first plurality of teeth and the second plurality of teeth are at least partially embedded into tissue on the first bone. The first plurality of teeth and the second plurality of teeth cause the first implant component to resist movement with respect to the first bone after implantation.

Another embodiment of the invention is directed to a method of resurfacing a joint with a low friction resurfacing implant system. The joint includes a first bone and a second bone that are adjacent to each other and movable with respect to each other.

A first implant component is provided that includes a first bearing surface. A first visualization marker is positioned with respect to the first bearing surface. The first visualization marker has a first marker section and a second marker section. The first marker section is oriented at an angle with respect to the second marker section.

The first implant component is implanted between the first bone and the second bone. A location and an orientation of the first implant component are determined using an imaging technique that locates the first visualization marker.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE PREFERRED EMBODIMENTS

The present invention provides an implantable joint prosthesis configured to resurface a natural articular joint, tools, and methods for implantation. The prosthesis may include a first implant component and a second implant component. The first implant component may be implantable on a first bone and may have a first bearing surface. The second implant component may be implantable on a second bone and have a second bearing surface that corresponds to the first bearing surface.

Each bearing surface may include a flattened section such that when the bearing surfaces are placed in cooperation with one another in a preferred orientation, the flattened sections are aligned. Alternatively, the bearing surfaces may have an asymmetric configuration, with non-congruent surfaces working cooperatively. The implant corrects joint deformity by providing new articulating surfaces. The articulating surfaces restore a low coefficient of friction as well as improved fatigue, wear and loading characteristics for the joint.

Figure 1:
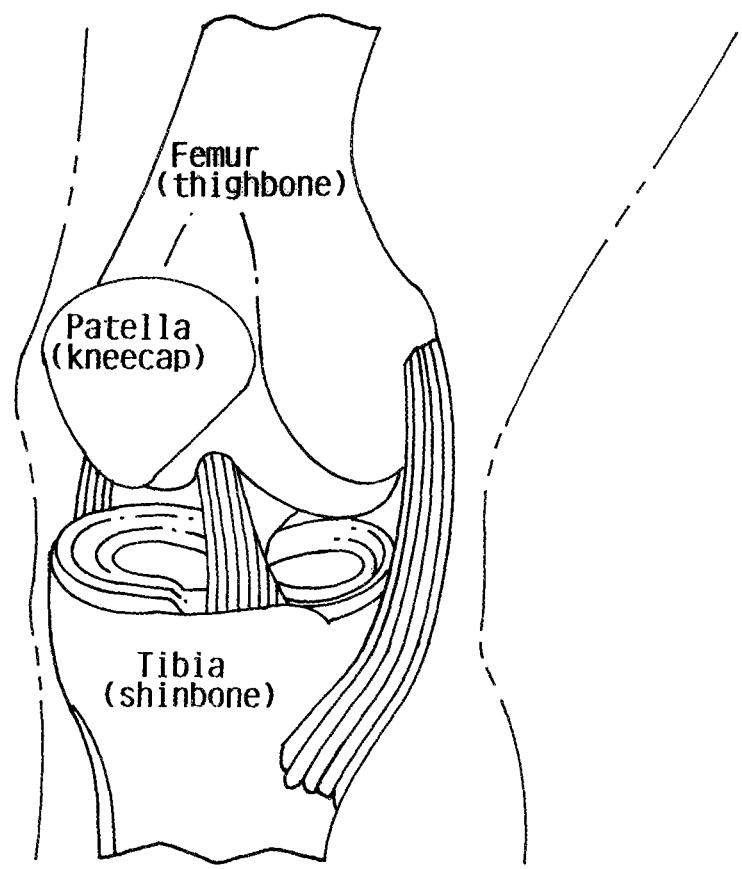
FIG. 1 is a simplified view of the anatomy of the human knee joint illustrating the area in which the systems and methods of the present disclosure are useful in treating.
Figure 2:
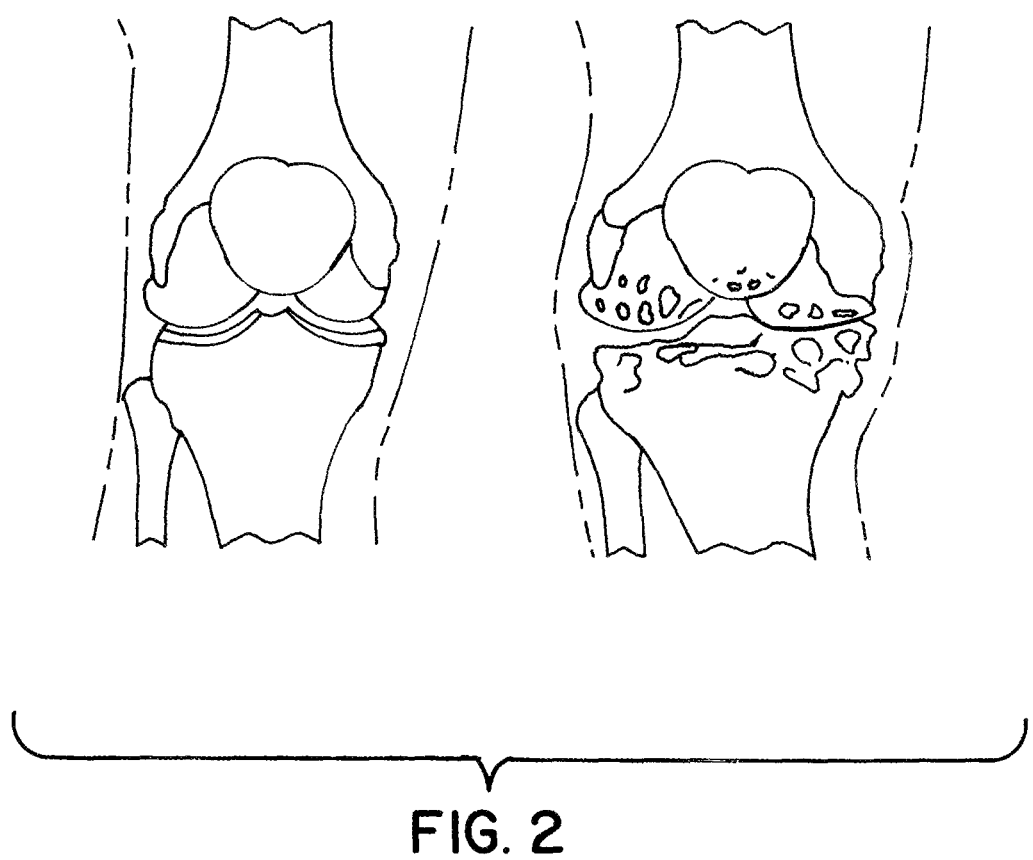
FIG. 2 is a simplified view of a healthy vs. osteoarthritic bone, cartilage and meniscus of the knee.
Figure 3:
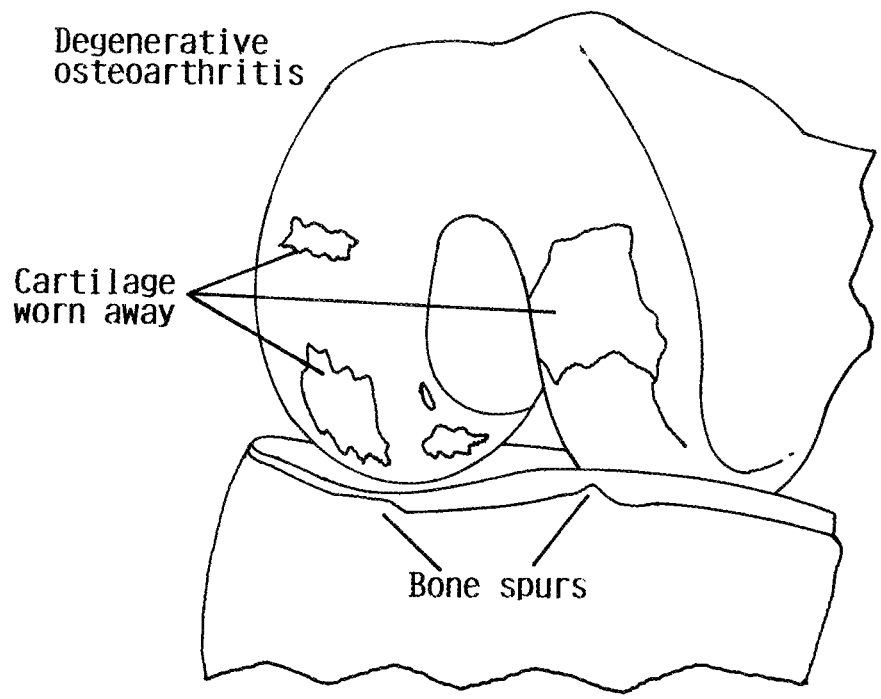
FIG. 3 is a detailed view of osteoarthritis of the knee.

The structure of the human knee is illustrated in FIG. 1. FIG. 2 illustrates a comparison of the healthy knee cartilage and meniscus, which is illustrated on the left, versus a severely osteoarthritic knee cartilage and meniscus, which is illustrated on the right. The severely osteoarthritic knee illustrated would likely require total knee replacement surgery. FIG. 3 also illustrates a knee joint with severely osteoarthritic knee cartilage.

Since total knee implants typically last for only 10-15 years, a patient generally cannot receive such an implant until they are at least 75 years of age. Since pain will be experienced by the patient long before the knee becomes as severely arthritic, as illustrated in FIG. 2, the present invention serves to reduce the pain level in the knee(s) of the patient until they reach an appropriate age for partial or total knee replacement surgery.

Referring to FIGS. 4-12, preferred embodiments of the invention are illustrated. The components of the implantable prosthesis are configured to be kidney-shaped, round, oval or c-shaped discs to provide resurfacing of the articular cartilage and/or menisci of corresponding mating surfaces existing in the knee joint. The selection of these component shapes are directed towards accommodating the passage of the anterior cruciate ligament through the knee joint space.

The inner and outer sides of the knee joint are referred to as lateral and medial. Lateral meaning the outside of the knee along the side of the body, and medial meaning the inside of the knee closest to the centerline of the body. One implant component resurfaces the lateral femoral condyle and the corresponding mating implant component resurfaces the lateral tibial plateau.

Likewise, the medial femoral condyle and medial tibial plateau would be resurfaced in a similar fashion. The surface contouring and flexibility of the components enable them to function together as did the native meniscus and the articular surfaces lying between the femoral condyle and tibial plateau prior to developing OA.

FIGS. 4-9 indicate only one-half of the two resurfacing components of the lateral tibial/meniscal plateau and only one-half of the two components of the medial tibial/meniscal plateau (medial being the larger of the two).

Figure 4:
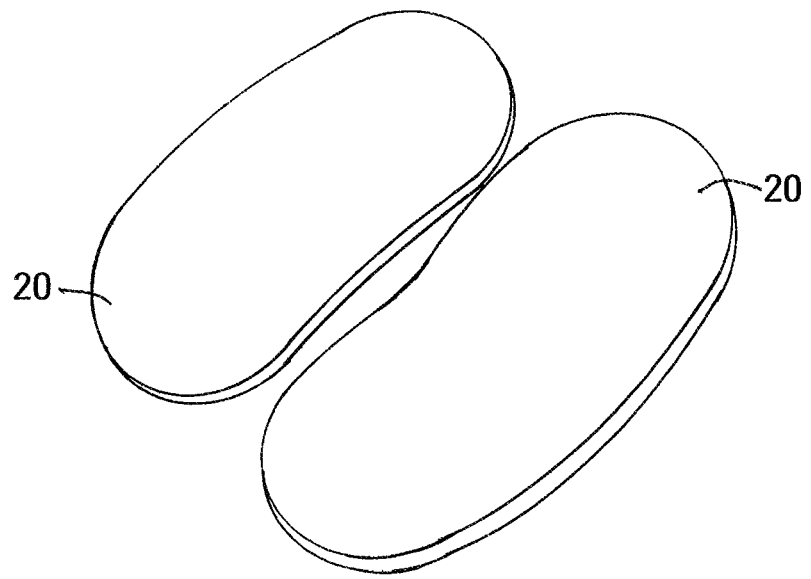
FIG. 4 is a preferred embodiment of the invention indicating one half of the lateral compartment two-component implant and one half of the medial compartment two-component implant.

FIG. 4 illustrates two conformable implant components 20 that are shaped to match the contour of the femoral condyle surface and articulate smoothly with the corresponding lateral and medial tibial/meniscal components respectively.

Figure 5:
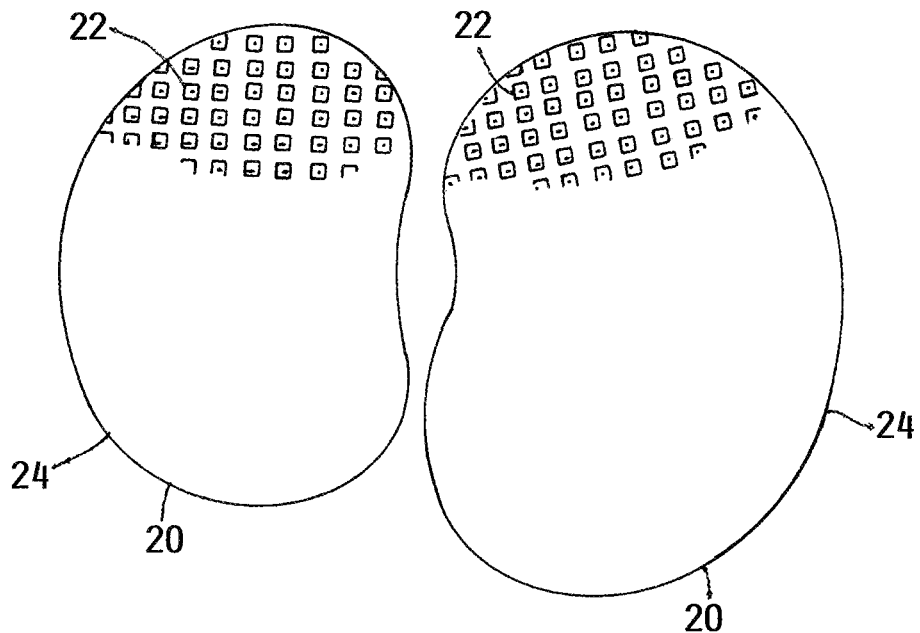
FIG. 5 is a reverse side of each half of the lateral and medial implants shown in FIG. 4 illustrating tissue engaging spikes.
Figure 6:
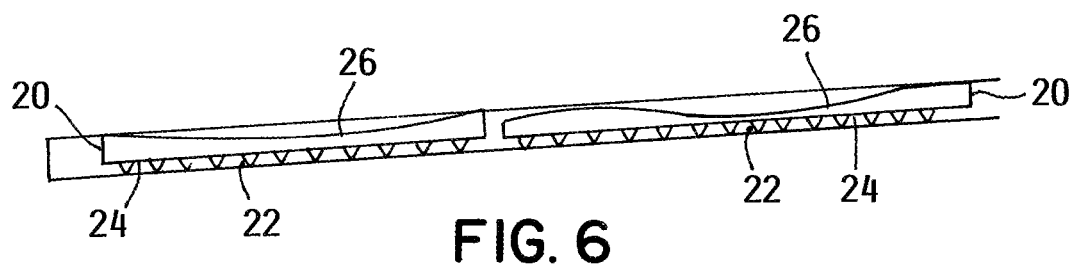
FIG. 6 is a cross-section indicating contour of articulating surfaces and spikes of FIGS. 4 and 5.

FIGS. 5 and 6 illustrate two conformable implant components 20 that have a shape, which is similar to the conformable implant components illustrated in FIG. 4, but which include mechanical engagement means 22.

The mechanical engagement means 22 include a plurality of teeth or spikes on that extend from an engagement surface 24 of the conformable implant components 20. The mechanical engagement means 22 will engage the articulating cartilage after the conformable implant component 20 is implanted.

Figure 11:
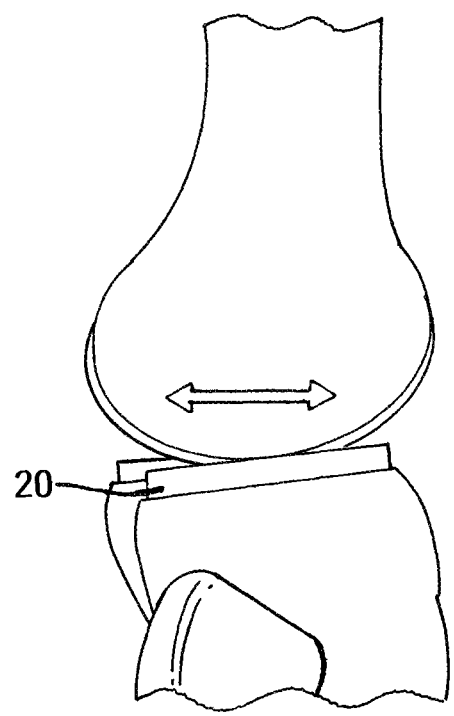
FIG. 11 is a side view of implanted components in knee joint.
Figure 12:
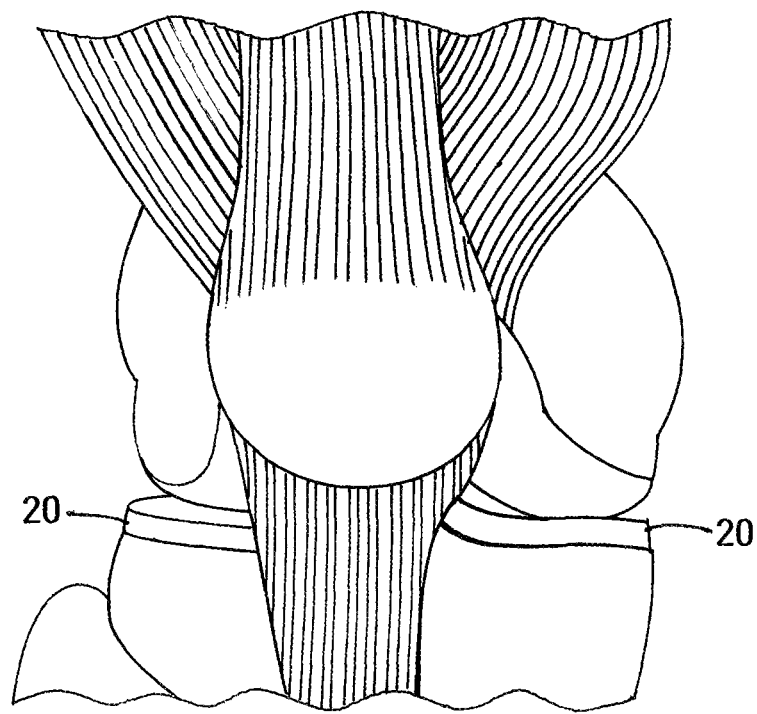
FIG. 12 is a front view of implanted components in knee joint.

The mechanical engagement means 22 thereby reduces the potential of the conformable implant component moving with respect to the knee joint after implantation. FIGS. 11 and 12 illustrate how all four components of the knee implant would appear in the joint if both lateral and medial aspects were resurfaced.

As illustrated in FIGS. 5 and 6, the mechanical engagement means 22 may be positioned over substantially all of the engagement surface 24. In certain embodiments, the mechanical engagement means 22 is fabricate from the same material as the other portions of the conformable implant component 20.

In other embodiments, the mechanical engagement means 22 is fabricated separately from the other portions of the conformable implant component 20 and then attached to the conformable implant component 20 during the manufacturing process.

As illustrated in FIG. 6, the teeth proximate the middle of the conformable implant component 20 may have a length that is greater than the teeth proximate the edges of the conformable implant component 20.

Opposite the engagement surface 24 is the articulating surface 26. When two conformable implant components 20 are implanted in an adjacent relationship, the articulating surfaces 26 on the adjacent conformable implant components 20 are positioned adjacent to each other. When the joint is moved after implant of the conformable implant components, the articulating surfaces 26 may slide with respect to each other.

A patient with an osteoarthritic knee may need only one side of the knee joint resurfaced. The medial side of the osteoarthritic knee tends to deteriorate faster than the lateral side. The preferred embodiments of the invention may be implanted on one or both sides of the knee joint. Although the peripheral outline of the implants is anticipated to remain the same, variations in implant overall height may be required depending on the patient's procedural requirements.

Each of the resurfacing bodies exhibits sufficient flexibility to transition from a relatively flat state to an inserted state in which the resurfacing body substantially matches any multiplanar curvatures and concavities of the corresponding knee joint articular face in the presence of compressive forces associated with a typical, adult human knee joint.

With this construction, the system is capable of establishing a new sliding interface within the knee joint via articulating surfaces of the resurfacing bodies, thereby eliminating the pain-causing, bone-on-bone articular interface associated with the natural anatomy. Further, by conforming to the natural shape associated with the native knee joint articular faces, the system of the present disclosure can be inserted on a minimally-invasive basis, and restructuring (e.g., removal) of the natural bony interface is not required.

Once inserted, the surfaces of the conformable implants are formed to coapt and provide smooth articulation. Surface coaptation and articulation are accomplished by providing concave and convex aspects on the mating portions of each of the tibial/meniscal and femoral components.

It is imperative the implant discs are securely fastened into the knee joint while maintaining smooth articulating surface interaction during the loading and motion demands typically placed on the knee. Implant discs therefore may be attached to the articular cartilage of the tibia or femoral condyle with mechanical engagement. Mechanical engagement may include providing the surface of the two implant components in contact with the articular cartilage with teeth or spikes. The base web defines opposing major surfaces. The teeth and the base web define the overall height of the device.

Despite the engagement of a plurality of teeth with the articular cartilage, additional or alternative mechanical engagement may also include capped edges, side tabs or flats secured with bone cement or fixation devices such as screws. FIGS. 7-10 indicate some of the various configurations anticipated to enable additional mechanical securement of implant components to the articular cartilage.

Figure 7:
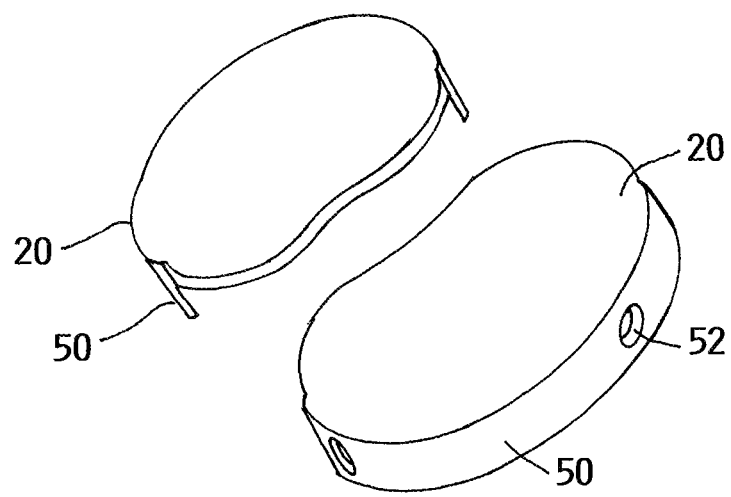
FIG. 7 is a perspective view of implants having cap feature with side holes.

The embodiment shown in FIG. 7 includes a folded over edge creating a cap 50 that extends along at least a portion of an edge of the conformable implant component 20. The cap 50 may have at least one hole 52 formed therein that is adapted to receive a screw (not shown) that is extended into the bone (not shown) to retain the conformable implant component 20 in a substantially stationary position with respect to the bone.

Figure 8:
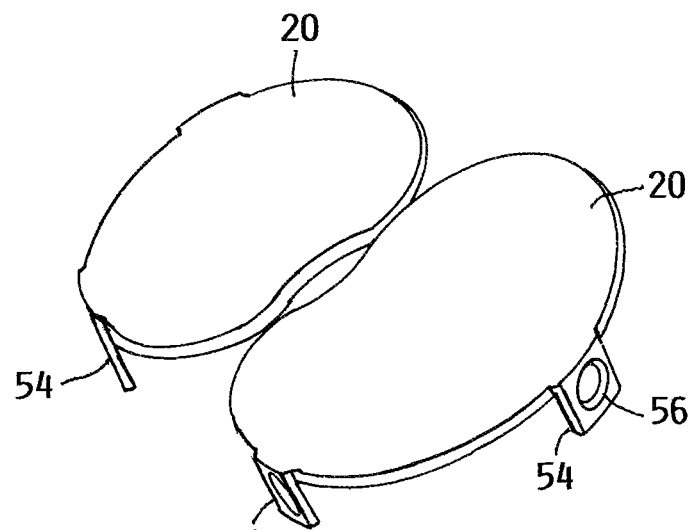
FIG. 8 is a perspective view of implants having tab feature.

FIG. 8 illustrates an alternative configuration for mounting the conformable implant component 20 with respect to the bone (not shown) using a plurality of tabs 54. The tabs may be positioned in a spaced-apart configuration around the conformable implant component 20. Each of the tabs 54 may have an aperture 56 formed therein that is adapted to receive a screw (not shown) affixing the conformable implant component 20 to the bone.

Figure 9:
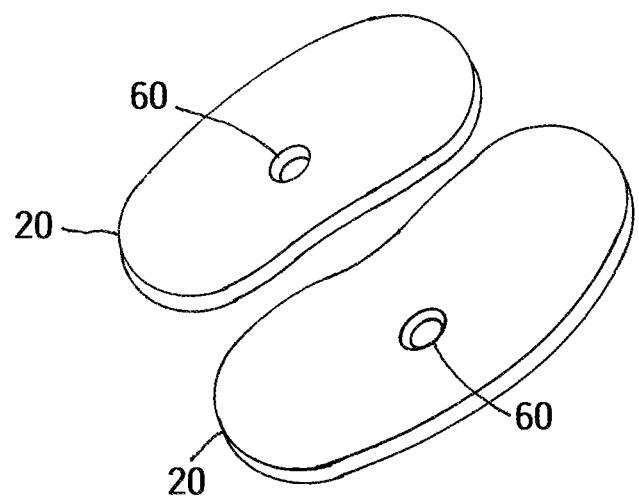
FIG. 9 is a perspective view of implants having top center hole feature.
Figure 10:
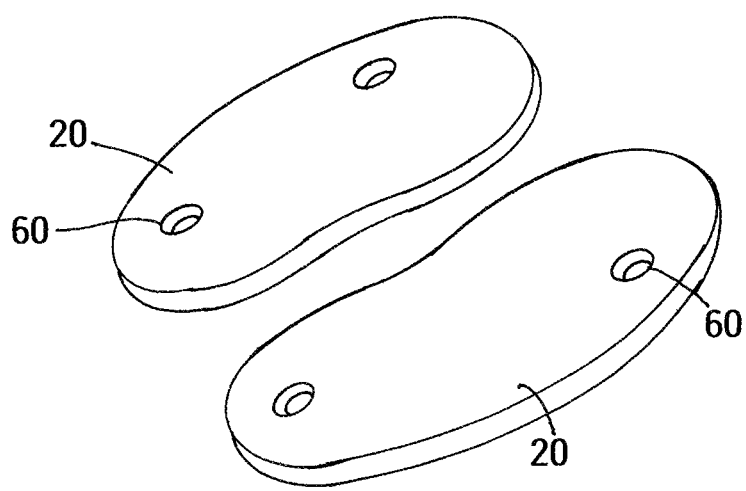
FIG. 10 is a perspective view of implants having top dual hole feature.

FIGS. 9 and 10 illustrate the conformable implant component 20 having at least one hole 60 formed therein. Similar to the other embodiments, the hole 60 is adapted to receive a screw (not shown) for affixing the conformable implant component 20 to the bone.

FIGS. 9 and 10 would be more feasible in the femoral condyle application as securement configurations due to the nature of the convex surface of the condyle when accessing the knee joint from the periphery of the knee in a minimally invasive or less-invasive setting. All of the embodiments would be conducive to receiving bone cement or adhesive in addition to screws to assist in fixation of the implants to the articular cartilage/bone.

Other preferred embodiments of the present invention include providing an implant configured for placement in the articulating joint between the patella and the femur (not shown). A patellar-femoral implant configuration would be a round disc rather than kidney or c-shaped.

In the preferred embodiments the overall height (or thickness) of the implant is anticipated to be consistent along its length and width.

Alternatively, the overall height may taper from one end to the other or be variable at different locations along the length and width of the implant depending on the variability existing in the diseased knee joint. The important factors are that the two-components of each pair maintain a low-friction conformable interface. In any case, the resurfacing implants are anticipated to have an overall height that ranges from 0.5-10 mm.

Yet other aspects in accordance with principles of the present disclosure relate to a kit for treating a knee joint of a patient. The kit includes a treatment system as described above (e.g., a superior resurfacing device having a superior resurfacing body, and an inferior resurfacing device having an inferior resurfacing body), along with an insertion tooling set.

The insertion tooling set includes a delivery cannula and an elongate pusher tool. The delivery cannula has a distal end and defines an internal passage that is open at the distal end. The pusher tool is sized to be slidably received within the passage.

With this construction, the kit is configured to provide an insertion arrangement in which the resurfacing devices and the pusher tool are slidably received within the passage, with the resurfacing devices being stacked against one another adjacent the distal end and a distal region of the pusher tool abutting the resurfacing devices opposite the distal end of the cannula. In some embodiments, the resurfacing devices each form a notch sized to receive a finger formed by the pusher tool to achieve selective engagement therebetween.

The biocompatibility and biodurability requirements narrow the material options available for weight bearing implantable devices. Biocompatibility and biodurability are essential for permanent medical implants. The material choice cannot incite reactions such as cytotoxicity, systemic toxicity, irritation, macroscopic or allergic reactions, and muscle degeneration. The implant component materials are required to have high fatigue resistance and strength. Important material property considerations include yield strength, break strength, flexural strength, shear strength, and compressive strength.

Considering these performance requirements, the low-friction knee resurfacing implant is preferably made of medical grade polyetheretherketone (PEEK). Polyetheretherketone is an engineering thermoplastic which has been used in certain medical implant applications such as bone screws, as a component for implant medical leads and for spinal fusion cages.

It is available in pure form and also in other formulations containing additives such as carbon fiber, barium sulphate and glass fiber. Additionally the material is available as a composite comprising a PEEK matrix containing, glass and short or continuous carbon fibers for applications requiring even greater strength and rigidity. The terms "PEEK material," or "PEEK-type material" as referenced are to include all materials of the polyaryletherketone family such as PEEK (Polyetheretherketone), PAEK (polyaryletherketone), PEK (polyetherketone), PEKK (polyetherketoneketone), PEKEKK (polyetherketoneetherketoneketone), PEEKK (polyetheretherketoneketone), and PAEEK (polyaryletheretherketone). The PEEK material selected may include the use of fillers or additives such as nanocomposites, or glass/carbon fibers.

The use of PEEK material disclosed in accordance with the preferred embodiment of the invention thus provides an implant for the knee that has a low coefficient of friction, is strong and durable, and having radiolucent properties to not interfere with imaging of the joint area. Implants made from PEEK can be repeatedly steam and gamma sterilized with no detrimental effects. These implants are inert or highly resistant to chemical attack.

Other biocompatible materials may also be used in other embodiments where the knee joint resurfacing is a temporary need, such as in sports injuries where the damaged joint slowly regenerates. One such material is a product currently under research by a company called Oxford Biomaterials. Oxford Biomaterials is developing a silk-based product called SilkBone.

SilkBone has been approved for use in humans and has mechanical load bearing properties similar to human bone with compressive forces up to 20 MPa. SilkBone is a composite of silk proteins and the natural mineral component of human bone, hydroxyapatite. An articulating joint implant having the strength and low-coefficient of friction properties of a silk-based material is additionally anticipated.

The radiolucent aspects of the PEEK material implants of the present invention may include one or more radiographic markers that are detectable by X-ray or other imaging techniques to assist in the positioning the implant during the minimally invasive surgery and to monitor its location post-implantation. Typically, these markers will be encased in predetermined locations in the implant at their periphery. Coatings that create subtle outline of the implant device during imaging may also be used, or additives such as Barium Sulphate may be included to provide some radiopacity to the implant.

Figure 13:
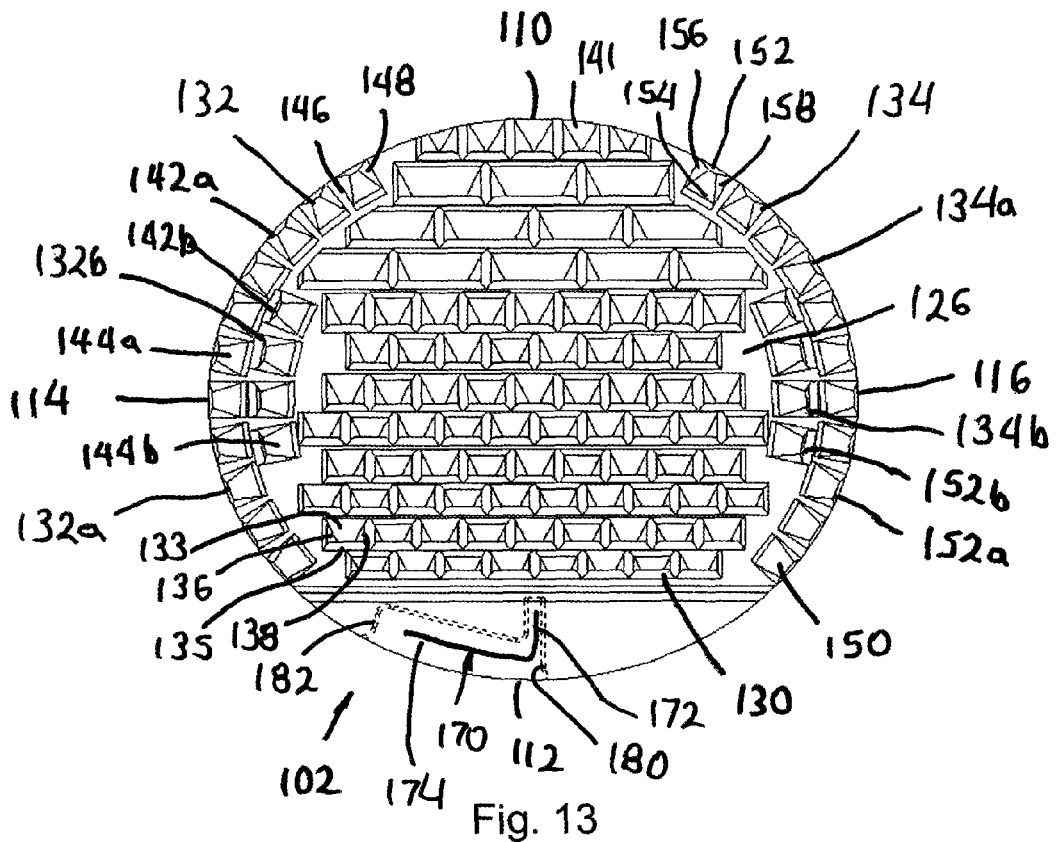
FIG. 13 is a top view of an alternative embodiment of the implant.
Figure 14:
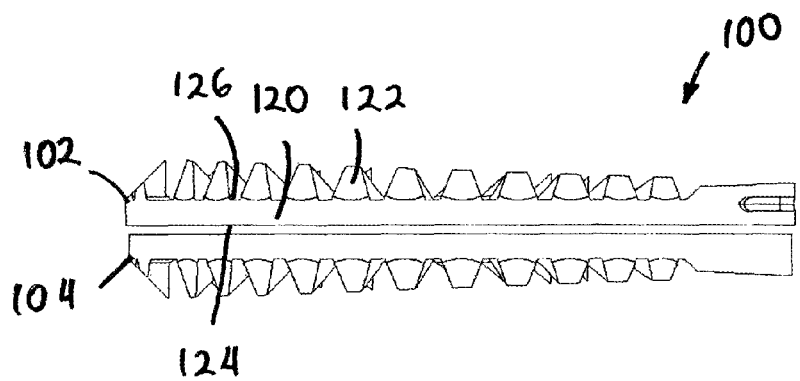
FIG. 14 is a side view of two of the implants of FIG. 13 positioned in an insertion orientation.

Another embodiment of the invention is directed to an implant system 100, as illustrated in FIGS. 13-16. In certain embodiments, the implant system 100 includes a superior resurfacing device 102 and an inferior resurfacing device 104, as illustrated in FIG. 14.

The superior resurfacing device 102 serves as a liner for a lower end of the femur and the inferior resurfacing device 104 serves as a liner for an upper end of the tibia similar to the embodiment illustrated in FIG. 11. In certain embodiments, the resurfacing devices 102, 104 are capable of conforming to the naturally-occurring shape or curvature of the knee joint anatomy.

The resurfacing devices 102, 104 thereby replace a bone-on-bone interface caused by degradation of the natural joint in a manner achieving normal or near normal mobility of the joint. It is also possible to use the concepts of the invention in conjunction with other articular joints.

The superior resurfacing device 102 and the inferior resurfacing device 104 may each have a substantially similar shape. As such, the description herein is provided with respect to the superior resurfacing device 102.

Figure 15:
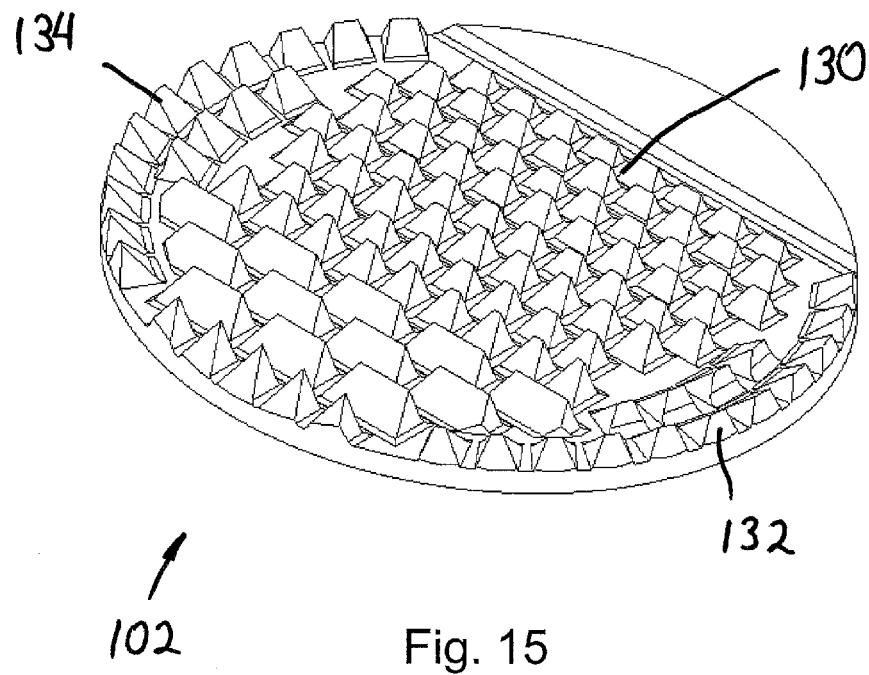
FIG. 15 is a first perspective view of the implant of FIG. 13.
Figure 16:
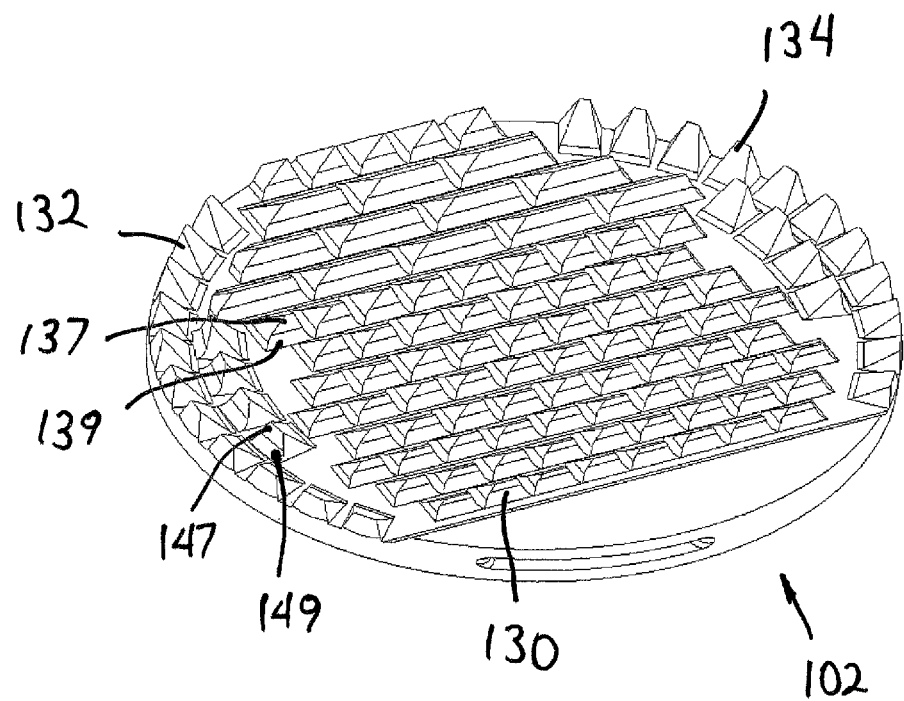
FIG. 16 is a second perspective view of the implant of FIG. 13.

While FIGS. 13, 15 and 16 illustrate that the superior resurfacing device 102 has a disc-like shape, it is possible for the superior resurfacing device 102 to have other shapes using the concepts of this invention. For example, the superior resurfacing device 102 may be formed in two components that are similar to the shape of the resurfacing devices illustrated in FIG. 5. In such a configuration, each of the superior device components may at least partially be formed in a kidney bean shape.

The superior resurfacing device 102 may be defined as having a leading edge 110, a trailing edge 112, a first opposing side 114 and a second opposing side 116. The leading edge 110 is on the end of the superior resurfacing device 102 that is intended to be inserted first during the implantation process.

The trailing edge 112 may be oriented generally opposite from the leading edge 110. As such, the trailing edge 112 is the end of the superior resurfacing device 102 that enters a bodily space last during the implantation process.

The first opposing side 114 and the second opposing 116 are located on opposite edges of the superior resurfacing device 102. The first opposing side 114 and the second opposing side 116 extend between the leading edge 110 and the trailing edge 112.

The superior resurfacing device 102 may include a base web 120 and a plurality of teeth 122 that extend from the base web 120. The base web 120 defines opposing major surfaces that include a first major surface 124 and a second major surface 126.

In certain embodiments, the base web 120 may be formed with a relatively uniform thickness. In other embodiments, the base web 120 is tapered such that proximate the leading edge 110, the base web 120 is thicker than proximate the trailing edge 112. In certain embodiments, the angle of the taper is up to about 4 degrees. In other embodiments, the angle of the taper is about 2 degrees.

The first major surface 124 may be generally smooth to serve as an articulating surface, which articulates relative to a corresponding articulating surface of the inferior resurfacing device 104 when the first major surfaces 124 on the superior resurfacing device 102 and the inferior resurfacing device 104 are positioned adjacent to each other as illustrated in FIG. 14.

As such, the first major surface 124 can be referred to as the "articulating surface" of the superior resurfacing device 102. In certain embodiments, the articulating surface 124 may be coated with a separate layer that provides enhanced frictional (i.e., lower coefficient of friction) and/or wear characteristics.

The plurality of teeth 122 project from the second major surface 126 in a direction generally opposite the first major surface 124. In certain embodiments, the plurality of teeth 122 may include at least two groups of teeth. The teeth in each group of teeth may be shaped differently, oriented in a different direction and/or aligned differently than the teeth in the other groups of teeth.

While the description below is provided with respect to a particular configuration of teeth that is illustrated in the figures, a person of skill in the art will appreciate that various other configurations of teeth may be used that incorporate the concepts discussed below to reduce the potential of the superior and inferior resurfacing devices 102, 104 moving after implantation.

An important aspect of the teeth 122 is that they minimize the movement of the superior and inferior resurfacing devices 102, 104 with respect to the adjacent tissue. Such movement can include sliding out of the joint in which the superior and inferior resurfacing devices 102, 104 are implanted. Such movement can also include rotation of one of more of the superior and inferior resurfacing devices 102, 104 in the joint where the superior and inferior resurfacing devices 102, 104 are implanted.

The first set of teeth 130 may resist movement of the superior resurfacing device 102 towards the trailing edge 112 such that the superior resurfacing device 102 moves out of the implant region in a direction that is opposite of the direction in which the superior resurfacing device 102 moved during the implantation process.

The first set of teeth 130 may be positioned at an intermediate location on the base web 120. As used herein, intermediate location means that the first set of teeth 130 is not located proximate the first opposing side 114 and the second opposing side 116. The first set of teeth 130 may also not be located proximate to the trailing edge 112. In certain embodiments, the first set of teeth 130 are positioned proximate the leading edge 110.

Alternatively, the first set of teeth 130 may be positioned to substantially cover the second major surface 126 such that the first set of teeth 130 are located proximate to the first opposing side 114 and the second opposing side 116.

The first set of teeth 130 may be positioned in a plurality of rows. These rows may be oriented generally transverse to a direction in which the superior resurfacing device 102 moves during the insertion process.

The teeth in adjacent rows of the first set of teeth 130 may be offset as most clearly illustrated in FIG. 13. In certain embodiments, the teeth in a first row are placed so that the edges of the teeth in the first row are approximately aligned with a center of the teeth in a second row.

Using such a configuration of teeth enhances the ability of the superior resurfacing device 102 to resist movement after implantation because if the teeth in the first row cut a path through the tissue into which the teeth extend, the teeth in the second row will not also pass through the same path in the tissue. Rather, the teeth in the second row will have to cut a separate path through the tissue into which the teeth extend. Such a process requires more force than if the teeth in the second row move through the path formed in the tissue by the first row of teeth.

Alternatively or additionally, at least a portion of the teeth in the first set of teeth 130 may have a greater width. As used herein, width of the teeth is a direction that is generally perpendicular to the direction between the leading edge 110 and the trailing edge 112.

The teeth 130 having the greater width may also enhance the ability of the superior resurfacing device 102 to resist movement after implantation because the teeth 130 having the greater width engage the tissue over a larger area than the other teeth having a smaller width. In one such configuration, the teeth 130 with a greater width have a width that is about twice as large as the width of the teeth in the other portion of the first set of teeth 130.

The wider teeth 130 may also exhibit a greater resistance to deformation when subjected to a load placed thereon such as when it is attempted to slide the superior resurfacing device 102 with respect to the tissue into which the teeth 130 are implanted. Such greater resistance to deformation reduces the potential that the teeth 130 will deform to an extent where the teeth fail and/or that the superior resurfacing device 102 is permitted to move with respect to the tissue into which the teeth 130 are implanted.

In certain embodiments, the teeth 130 with the greater width may be positioned closer to the leading edge 110 than the other teeth in the first set of teeth 130 that have a smaller width. The teeth 130 with the greater width may be provided in more than one row. In certain embodiments, there are at least two rows of teeth 130 having a greater width.

The teeth in the different rows of the first set of teeth 130 may be formed so that the teeth in the rows proximate the leading edge 110 have a depth that is greater than a depth of the teeth in the rows proximate the trailing edge 112, as illustrated in FIG. 14. As used herein, depth of the teeth is a direction that is generally perpendicular second major surface 126.

In certain embodiments, the teeth in the rows proximate the leading edge 110 have a depth that is between about 80 percent and about 120 percent greater than a depth of the teeth in the rows proximate the trailing edge 112.

There may also be at least one intermediate row of teeth having a depth that is less than the depth of the teeth in the rows proximate the leading edge 110 and having a depth that is greater than the depth of the teeth in the rows proximate the trailing edge 112.

The teeth in the first set of teeth 130 may each have a leading face 133 and a trailing face 135. The leading face 133 is oriented towards the leading edge 110 while the trailing face 135 is oriented towards the trailing edge 112. An angle formed between the trailing face 135 and the base web 120 is greater than an angle formed between the leading face 133 and the base web 120.

In certain embodiments, the angle formed between the leading face 133 and the base web 120 may be between about 20° and about 60°. In other embodiments, the angle formed between the leading face 133 and the base web 120 may be between about 30° and about 50°.

In certain embodiments, the angle formed between the trailing face 135 and the base web 120 may be between about 75° and about 105°. In other embodiments, the angle formed between the trailing face 135 and the base web 120 may be about 90°.

The teeth may also include a first side surface 136 and a second side surface 138. An angle formed between the first side surface 136 and the base web 120 may be between about 40° and about 80°. In other embodiments, the angle formed between the first side surface 136 and the base web 120 may be between about 60° and about 80°. The second side surface 138 may be oriented at an angle with respect to the base web 120 that is about the same as the angle between the first side surface 136 and the base web 120.

In other embodiments, the trailing face 135 may include an upper tooth section 137 and a lower tooth section 139 that are oriented in a non-collinear orientation with respect to each other, as illustrated in FIG. 16. In certain embodiments, an obtuse angle is formed between the upper tooth section 137 and the lower tooth section 139. In other embodiments, the angle between the upper tooth section 137 and the lower tooth section 139 is between about 135° and 170°.

As a result of this configuration, the upper tooth section 137 may be oriented at an angle with respect to the base web 120 that is greater than an angle between the lower tooth section 139 and the base web 120.

The first set of teeth 130 may include a plurality of leading edge teeth 141 that are positioned along the leading edge 110, as illustrated in FIGS. 13, 15 and 16. The teeth in the plurality of leading edge teeth 141 may have a width and a depth that is similar to the teeth positioned proximate to a center of the superior resurfacing device 102.

First and second side surfaces of the leading edge teeth 141 may be oriented at a smaller angle than the teeth positioned proximate to the center of the superior resurfacing device 102. This configuration provides the teeth in the leading edge teeth 141 with a pointier configuration than the other teeth in the first set of teeth 130.

Because the leading edge teeth 141 are positioned along the leading edge 110 and because of the curvature of the leading edge 110, the teeth in the leading edge teeth 141 may not all have the same depth, as most clearly illustrated in FIG. 13.

The second set of teeth 132 and the third set of teeth 134 enhance the ability of the superior resurfacing device 102 to resist being displaced side-to-side after implantation. Such movement may be in a direction that is angularly offset with respect to a direction in which the superior resurfacing device 102 moves during the implantation process.

While it is possible for the movement to be generally perpendicular to the direction in which the superior resurfacing device 102 moves during the implantation process, the second set of teeth 132 and the third set of teeth 134 may also prevent movement of the superior resurfacing device 102 in other directions that are not perpendicular to the direction in which the superior resurfacing device 102 moves during the implantation process.

The second set of teeth 132 are formed at or along the first opposing side 114. The individual teeth 140 in the second set of teeth 132 may be formed with a non-symmetrical relationship with respect to the teeth in the first set of teeth 130.

The second set of teeth 132 may be arranged in a plurality of rows. In certain embodiments, the second set of teeth 132 includes a first row of teeth 132a and a second row of teeth 132b. The first row of teeth 132a is positioned along the first opposing side 114. The second row of teeth 132b may be positioned between the first row of teeth 132a and the first set of teeth 130.

While it is illustrated that the teeth in the second set of teeth 132b are generally aligned with the teeth in the first set of teeth 132a, in certain embodiments, the teeth in the second set of teeth 132b may be offset from the teeth in the first set of teeth 132a similar to the manner in which adjacent rows of teeth in the first set of teeth 130 are offset from each other.

The second teeth 140 in the first row of teeth 132a may each have an exterior face 142a and an interior face 144a. The exterior face 142a faces the first opposing side 114 while the interior face 144a faces the second opposing side 116. An angle formed between the interior face 144a and the base web 120 is less than an angle formed between the exterior face 142a and the base web 120.

In certain embodiments, the angle formed between the exterior face 142a and the base web 120 may be between about 75° and about 105°. In other embodiments, the angle formed between the exterior face 142a and the base web 120 may be about 90°.

In certain embodiments, the angle formed between the interior face 144 and the base web 120 may be between about 20° and about 60°. In other embodiments, the angle formed between the interior face 144 and the base web 120 may be between about 30° and about 50°.

The second teeth 140 may also include a first side surface 146 and a second side surface 148. An angle formed between the first side surface 146 and the base web 120 may be between about 40° and about 80°. In other embodiments, the angle formed between the first side surface 146 and the base web 120 may be between about 60° and about 80°. The second side surface 148 may be oriented at an angle with respect to the base web 120 that is about the same as the angle between the first side surface 146 and the base web 120.

The teeth in the second row of teeth 132b may be shaped similarly to the teeth in the first row of teeth 132a in most respects. In one configuration, an angle between the exterior face 142b of the teeth in the second row of teeth 132b and the base web 120 may be less than an angle between the exterior face 142a of the teeth in the first row of teeth 132a and the base web 120.

In certain embodiments, the angle formed between the exterior face 142b of the teeth in the second row of teeth 132b and the base web 120 may be between about 60° and about 80°.

In other embodiments, the exterior face 142b of the teeth in the second row of teeth 132b includes an upper tooth section 147 and a lower tooth section 149 that are oriented in a non-collinear orientation with respect to each other. In certain embodiments, an obtuse angle is formed between the upper tooth section 147 and the lower tooth section 149.

As a result of this configuration, the upper tooth section 147 may be oriented at an angle with respect to the base web 120 that is greater than an angle between the lower tooth section 149 and the base web 120.

The third set of teeth 134 are formed at or along the second opposing side 116. The individual teeth 150 in the third set of teeth 134 may be formed with a non-symmetrical relationship with respect to the teeth in the first set of teeth 130.

The third set of teeth 134 may be arranged in a plurality of rows. In certain embodiments, the third set of teeth 134 includes a first row of teeth 134a and a second row of teeth 134b. The first row of teeth 134a is positioned along the second opposing side 116. The second row of teeth 134b may be positioned between the first row of teeth 134a and the first set of teeth 130.

While it is illustrated that the teeth in the second row of teeth 134b are generally aligned with the teeth in the first row of teeth 134a, in certain embodiments, the teeth in the second row of teeth 134b may be offset from the teeth in the first row of teeth 134a similar to the manner in which adjacent rows of teeth in the first set of teeth 130 are offset from each other.

The third teeth 150 in the first row of teeth 134a each have an exterior face 152 and an interior face 154. The exterior face 152 face the second opposing side 116 while the interior face 154 faces the first opposing side 114. An angle formed between the interior face 154 and the base web 120 is less than an angle formed between the exterior face 152 and the base web 120.

In certain embodiments, the angle formed between the exterior face 152 and the base web 120 may be between about 75° and about 105°. In other embodiments, the angle formed between the exterior face 152 and the base web 120 may be about 90°.

In certain embodiments, the angle formed between the interior face 154 and the base web 120 may be between about 20° and about 60°. In other embodiments, the angle formed between the interior face 154 and the base web 120 may be between about 30° and about 50°.

The third teeth 150 may also include a first side surface 156 and a second side surface 158. An angle formed between the first side surface 156 and the base web 120 may be between about 40° and about 80°. In other embodiments, the angle formed between the first side surface 156 and the base web 120 may be between about 60° and about 80°. The second side surface 158 may be oriented at an angle with respect to the base web 120 that is about the same as the angle between the first side surface 156 and the base web 120.

The teeth in the second row of teeth 134b may be shaped similarly to the teeth in the first row of teeth 134a in most respects. In one configuration, an angle between the exterior face 152b of the teeth in the second row of teeth 134b and the base web 120 may be less than an angle between the exterior face 152a of the teeth in the first group of teeth 134a and the base web 120.

In certain embodiments, the angle formed between the exterior face 152b of the teeth in the second row of teeth 142b and the base web 120 may be between about 60° and about 80°.

In other embodiments, the exterior face 152b of the teeth in the second row of teeth 134b includes an upper tooth section 157 and a lower tooth section 159 that are oriented in a non-collinear orientation with respect to each other. In certain embodiments, an obtuse angle is formed between the upper tooth section 157 and the lower tooth section 159.

As a result of this configuration, the upper tooth section 157 may be oriented at an angle with respect to the base web 120 that is greater than an angle between the lower tooth section 159 and the base web 120.

In some constructions, each tooth of the plurality of teeth can have an identical, or nearly identical, height. In other embodiments, the teeth can be formed with a tapered height such that the teeth proximate the leading edge 110 have a height that is greater than a height of the teeth proximate the trailing edge 112.

The height of the teeth may be tapered at an angle of up to about 4 degrees. In certain embodiments, the height of the teeth may be tapered at an angle of about 2 degrees. As a result of this configuration, the teeth proximate the leading edge 110 can establish a more rigid engagement with the corresponding tissue face to thereby resist displacement after insertion.

As described in greater detail below, a desired conformability characteristic of the superior resurfacing body 102 may be influenced by the overall thickness and the base web 120 to effectuate the desired degree of conformability. The overall thickness of the superior resurfacing body 102 may be selected by the treating clinician for insertion into a particular joint may vary as a function of other procedures associated with the insertion.

The conformability of the superior resurfacing device 102 may be enhanced by the layout of the teeth. In certain embodiments, the orientation of the first group of teeth 132 so that the teeth in adjacent rows are offset from each other may enhance the ability of the superior resurfacing device 102 to bend as compared to teeth configurations where teeth in adjacent rows are aligned with each other.

For example, the arrangement of the teeth in the offset configuration may provide the superior resurfacing device 102 with a greater number of folding axes than the configuration where teeth in adjacent rows are aligned with each other.

For example, where the superior resurfacing body 102 is inserted into a joint without any overt tissue removal prior to insertion, the overall thickness can be in the range of 0.5-2.5 mm. If, however, the insertion procedure entails first removing cartilage (or other tissue) from the joint, a thicker version of the superior resurfacing body 102 can be inserted, such that the overall thickness of the superior resurfacing body 102 is in the range of 0.5-3 mm.

The superior and inferior resurfacing devices 102, 104 may be integrally formed of a robust material that achieves desired conformability. The resurfacing body 46 in accordance with the present disclosure maintains its structural integrity (i.e., little or no wear) without adhesive or cohesive damage when subjected to typical articulation of the joint with movement of the patient.

In some constructions, the superior and inferior resurfacing devices 102, 104 are formed of an implantable-grade plastic, although other materials such as metal are also available. For example, the superior and inferior resurfacing devices 102, 104 can be made from the polyetherketone (PEK) family of plastics, which have strength, wear, flexibility, and biocompatibility properties appropriate for insertion into, and long-term functioning within, the joint.

Polyetheretherketone (PEEK) has surprisingly been found to provide not only the conformability attributes described below, but also long-term mechanical strength and resistance to wear. Additional material(s) can be incorporated, such as those exhibiting radio-opacity properties. For example, the superior and inferior resurfacing devices 102, 104 can be formed from a radio-opaque mineral (e.g., barium)-loaded PEK composition.

Visualization can also be provided via one or more radio-opaque marker bands (e.g., platinum marker band). The visualization marker 170 can be embedded within at least one of the superior and inferior resurfacing device 102, 104 (e.g., a radio-opaque rod inserted into a hole formed in the superior and inferior resurfacing device 102, 104). In another configuration, the radio-opaque material may be inserted along a portion of a perimeter of the superior and inferior resurfacing device 102, 104.

In another configuration of the visualization marker 170 indicates not only the location of the superior and inferior resurfacing device 102, 104 but also the orientation of the superior and inferior resurfacing device 102, 104 with respect to each other.

One such configuration of the visualization marker 170 includes two marker portions 172, 174 that are oriented at an angle with respect to each other. A first marker portion 172 may be oriented at an angle with respect to the second marker portion 174 that is between about 60 degrees and about 100 degrees. In certain embodiments, the angle between the first marker portion 172 and the second marker portion 174 is between about 70 degrees and about 80 degrees.

The first marker portion 172 may be positioned proximate to a central axis of the superior resurfacing device 102 that is intermediate the first opposing side 114 and the second opposing side 116.

An aperture 180 may be formed from the trailing edge 112 of the superior resurfacing device 102 that has a depth that is greater than a length of the first marker portion 172. The aperture 180 has a diameter that is slightly larger than the diameter of the first marker portion 172.

Adjacent to and intersecting with the aperture 180 is a channel 182 that has a length that is slightly larger than a length of the second marker portion 174. The channel 182 has a width that is slightly larger than the width of the second marker portion 174.

Forming the aperture 180 and the channel 182 with the preceding dimensions enables the visualization marker 170 to be recessed beneath the side of the superior resurfacing device 102 after insertion of the first marker portion 172 into the aperture 180 and the second marker portion 174 into the channel 182.

A sealant (not shown) may be placed over the visualization marker 170 to retain the visualization marker 170 in a stationary position with respect to the superior resurfacing device 102. The sealant should resist degradation after the superior and inferior resurfacing devices 102, 104 are implanted. The sealant should also be selected to minimize the potential of adverse interactions after the superior and inferior resurfacing devices 102, 104 are implanted.

Since the superior and inferior resurfacing devices 102, 104 are formed substantially similar to each other and the superior and inferior resurfacing devices 102, 104 are implanted with the articulating surfaces facing each other, the first marker portion in the superior and inferior resurfacing devices 102, 104 are aligned with each other during the insertion process.

In view of the preceding comments, if during evaluation of the position of the superior and inferior resurfacing devices 102, 104 using the visualization marker 170 indicates that the first marker portions 172 in the superior and inferior resurfacing device 102, 104 are not aligned with each other, it will be possible to determine that at least one of the superior and inferior resurfacing devices 102, 104 are not correctly oriented.

When the superior and inferior resurfacing devices 102, 104 are inserted correctly, the second marker portions 174 will be directed opposite from each other. The two visualization markers 170 thereby provide a generally T-shape. If the second marker portions 174 do not form the top of the T-shape using a radio-opaque detection technique, it can be determined that the superior and inferior resurfacing devices 102, 104 are not correctly inserted. For example, if the visualization markers 170 in the superior and inferior resurfacing devices 102, 104 form an L-shape, it can be determines that the articulating surface on the superior resurfacing device 102 is not facing the articulating surface on the inferior resurfacing device 104.

Depending on a thickness of the superior resurfacing device 102 proximate the trailing edge 112, there may not be teeth positioned on the superior resurfacing device 102 proximate the trailing edge 112, such as illustrated in FIGS. 13-16. For example, to accommodate the visualization marker 170, the base web 120 may need to be formed with a thickness proximate the trailing edge 112 than in the other portions of the superior resurfacing device 102 where the visualization marker 170 is not implanted therein.

The selected materials, shapes, and dimensions associated with the superior and inferior resurfacing devices 102, 104 impart or create a conformability property that allows the superior and inferior resurfacing devices 102, 104 to "match" the multi-planar concavity associated with a native joint articular face anatomy.

In general terms, "conformability" is inversely proportional to bending stiffness of the superior and inferior resurfacing device 102, 104 during insertion, and may be increased as the superior resurfacing device 102, 104 heats to body temperature and is allowed to creep.

With the above understandings in mind, the conformability characteristic of the superior and inferior resurfacing devices 102, 104 is sufficient such that the superior and inferior resurfacing devices 102, 104 readily transition from the relatively flat state illustrated in FIGS. 13-16 to an inserted state (not shown) in which the superior and inferior resurfacing devices 102, 104 substantially matches or mimics the naturally-occurring shape (e.g., radius of curvature of curved portions) of the joint face to which the superior and inferior resurfacing devices 102, 104 are secured. In this regard, the joint is subject to, or experiences, various loads that effectuate compressive forces at the region of interface between the superior and inferior articular faces.

Compressive loads normal to and across the articular faces will be generated upon separation/posterior translation of the superior articulating joint due to joint capsule tensioning. The conformable nature of the superior and inferior resurfacing devices 102, 104 is such that in the presence of these typical compressive forces, the superior and information resurfacing devices 102, 104 will transition from the relatively flat state to the inserted state in which the superior and inferior resurfacing devices 102, 104 substantially matches the geometry of the joint surface to which the superior and inferior resurfacing devices 102, 104 are secured (i.e., the superior and inferior resurfacing devices 102, 104 will flex to conform with a macroscopic shape/contour of the native articular face to which the superior and inferior resurfacing device 102, 104 are applied, but may not conform to the microscopic variations in the native articular face, for example small deviations due to cartilage defects, bony fissures, or small voids during preparation of the joint (typically 0.05-0.5 mm in width)).

This process will occur as the compressive forces applied by the ends of the hypothetical concave region of one articular surface (e.g., the superior articular surface) and the center of the corresponding convex surface on the opposing articular (e.g., the inferior articular surface) generate a bending moment on the superior and inferior resurfacing device 102, 104 that produces strain to conform the superior and inferior resurfacing devices 102, 104 to the native anatomy.

As used through this specification, a resurfacing device that conforms to the minimum radius of curvature of an adult human joint under normal physiologic forces (e.g., on the order of 180-450 N/mm per segment assuming a net 1 mm posterior shear translation) without deviations from the articular surface to which the resurfacing body is applied of greater than 1 mm is defined as being "conformable" and "substantially matching" the multi-planar curvatures of a joint.

Alternatively, a resurfacing body sized for placement within an adult human joint and exhibiting a Conformability Factor (described below) of not more than 100 N is also defined as being "conformable" and "substantially matching" the multi-planar curvatures of a joint in accordance with the present disclosure. In some embodiments, resurfacing bodies in accordance with the present disclosure exhibit a Conformability Factor of not more than 50 N, and in other embodiments not more than 25 N.

It has surprisingly been found that forming the superior and inferior resurfacing devices 102, 104 of PEEK and with the footprint size and thickness dimensions described above achieves the desired conformability characteristics, long-term resistance to wear, and joint stabilization following insertion.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A low friction resurfacing implant system comprising:
a first implant component comprising a first bearing surface and a first engagement surface located opposite the first bearing surface, wherein the first implant component has a leading edge and a trailing edge, wherein the first implant component comprises teeth that extend from the first engagement surface, wherein the teeth are arranged in a plurality of rows, wherein teeth in adjacent rows are offset from each other, wherein the first implant component further comprises a first opposing side and a second opposing side, wherein the first opposing side and the second opposing side each extend between the leading edge and the trailing edge and wherein the teeth comprise:
a first set of teeth proximate the first opposing side, wherein the first set of teeth each have an exterior face that faces the first opposing side and an interior face that faces the second opposing side;
a second set of teeth proximate the second opposing side, wherein the second set of teeth is oriented differently than the first set of teeth and wherein the second set of teeth each have an exterior face that faces the second opposing side and an interior face that faces the first opposing side; and
a third set of teeth between the first set of teeth and the second set of teeth, wherein the third set of teeth is oriented differently than the first set of teeth and the second set of teeth, wherein:
the first set of teeth comprises at least two rows of teeth, wherein the teeth in adjacent rows are offset from each other; and
the second set of teeth comprises at least two rows of teeth, wherein the teeth in adjacent rows are offset from each other.

2. The low friction resurfacing implant system of claim 1, and further comprising:
a second implant component having a second bearing surface and a second engagement surface located opposite the second bearing surface, wherein the second implant component comprises teeth that extend from the second engagement surface and wherein the second implant component has a shape that is substantially the same as the first implant component.

3. The low friction resurfacing implant system of claim 1, and further comprising:
a second implant component having a second bearing surface and a second engagement surface located opposite the second bearing surface, wherein the second implant component comprises teeth that extend from the second engagement surface and wherein the second implant component is substantially a mirror image of the first implant component.

4. The low friction resurfacing implant system of claim 1, wherein the first bearing surface comprises a flattened section.

5. The low friction resurfacing implant system of claim 1, wherein the first implant component is shaped to accommodate passage of an anterior cruciate ligament through a knee joint.

6. The low friction resurfacing implant system of claim 1, wherein the first implant component is shaped to at least partially conform to a shape of at least one of a lateral femoral condyle, lateral tibial plateau, a medial femoral condyle and a medial tibial plateau.

7. The low friction resurfacing implant system of claim 1, wherein the teeth comprise a first plurality of teeth and a second plurality of teeth, wherein the first plurality of teeth have a first width, wherein the second plurality of teeth have a second width and wherein the first width is greater than the second width.

8. The low friction resurfacing implant system of claim 1, wherein the first implant component includes an insertion axis that extends between the leading edge and the trailing edge, wherein teeth proximate the leading edge have a depth that is greater than a depth of teeth proximate the trailing edge and wherein depth is in a direction that is aligned with the insertion axis.

9. The low friction resurfacing implant system of claim 1, wherein the first implant component further comprises a first visualization marker that is fabricated from a radio-opaque material, wherein the first visualization marker comprises a first marker section and a second marker section and wherein the first marker section is oriented at an angle with respect to the second marker section.

10. The low friction resurfacing implant system of claim 1, wherein:
the first set of teeth is positioned along the first opposing side; and
the second set of teeth is positioned along the second opposing side.

11. The low friction resurfacing implant system of claim 1, wherein the teeth in the third set of teeth each have a leading face and a trailing face, wherein an angle between the trailing face and the first engagement surface is greater than an angle between the leading face and the first engagement surface.

12. The low friction resurfacing implant system of claim 1, wherein the teeth each have a leading face and a trailing face, wherein an angle between the trailing face and the first engagement surface is greater than an angle between the leading face and the first engagement surface.

13. The low friction resurfacing implant system of claim 12, wherein the angle between the leading face and the first engagement surface is between about 20° and about 60° and wherein the angle between the trailing face and the first engagement surface is between about 75° and about 105°.

14. The low friction resurfacing implant system of claim 12, wherein the trailing face comprises an upper section and a lower section and wherein the upper section extends from the lower section but is not collinear with the lower section.

* * * * *